United States Patent [19]

Häbich et al.

[11] Patent Number: 4,840,946
[45] Date of Patent: Jun. 20, 1989

[54] BENZAZOLYTHIO-CARBAPENEM ANTIBIOTICS

[75] Inventors: Dieter Häbich; Wolfgang Hartwig; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 119,752

[22] Filed: Nov. 12, 1987

[30] Foreign Application Priority Data

Nov. 28, 1986 [DE] Fed. Rep. of Germany ....... 3640715

[51] Int. Cl.$^4$ .................. A61K 31/40; C07D 487/04
[52] U.S. Cl. ..................................... 514/210; 542/350
[58] Field of Search ..................... 540/350; 514/210

[56] References Cited

FOREIGN PATENT DOCUMENTS 160876 11/1985 European Pat. Off. ............ 540/350
0170073 2/1986 European Pat. Off. ............ 540/350
0182213 5/1986 European Pat. Off. ............ 540/350

Primary Examiner—Robert Gerstl
Attorney, Agent, or Firm—Sprung, Horn, Kramer & Woods

[57] ABSTRACT

Antibiotically active benzazolylthio-carbapenems of the formula in which
$R^1$ represents hydrogen or a hydroxyl-protecting group,
$R^2$ represents hydrogen or a carboxyl-protecting group or an ester radical which can be cleaved off in vivo,
$R^3$ represents hydrogen or $C_1$–$C_{10}$-alkyl, $C_6$–$C_{12}$-aryl or $C_7$–$C_{14}$-aralkyl,
$R^4$ represents hydrogen or represents $C_1$–$C_{10}$-alkyl, $C_6$–$C_{12}$-aryl or $C_7$–$C_{14}$ aralkyl, or represents $C_1$–$C_{10}$-alkylsulphonyl, $C_6$–$C_{12}$-arylsulphonyl or $C_7$–$C_{14}$-aralkylsulphonyl, or represents an amino-protecting group, or represents a group of the formula in which
$R^5$, $R^6$ and $R^8$ are indentical or different and denote hydrogen, $C_1$–$C_{10}$-alkyl, $C_6$–$C_{12}$-aryl or $C_7$–$C_{14}$-aralkyl,
and
X represents O, S, NH or NCH$_3$,
or salts thereof.

10 Claims, No Drawings

BENZAZOLYTHIO-CARBAPENEM ANTIBIOTICS

The invention relates to amino-substituted benzoxazolylthio-, benzthiazolylthio- and benzimidazolylthiocarbapenem antibiotics, processes for the preparation thereof, and the use thereof as medicaments.

It is known that carbapenems of the thienamycin type [T. Kametani, Heterocycles 17, 463 (1982)] are distinguished by a good antibacterial action which also covers the majority of methicillin- and oxacillin-resistant Staphylococci [B. G. Christensen et al. in A. G. Brown & S. M. Roberts (eds), Recent Advances in the Chemistry of β-Lactam Antibiotics, Royal Society of Chemistry, Special Publication No. 52, 86 (1985)]. However, compounds such as thienamycin and imipenem have antibacterial weaknesses against certain Staphylococci and Enterococci; in addition, many derivatives of these compounds are unstable, as the monomeric substance, against degradation by the peptidases of the liver, specifically dehydropeptidase (I) (DHP-I) [H. Kropp et al., Antimicrob. Agents., Chemother. 22, 62 (1982)]. This enzyme is responsible for the metabolic deactivation of carbapenems and for the formation of toxic metabolites.

Benzazolylthio-carbapenem antibiotics of the general formula (I)

in which
- $R^1$ represents hydrogen or a hydroxyl-protecting group,
- $R^2$ represents hydrogen or a carboxyl-protecting group or an ester radical which can be cleaved off in vivo,
- $R^3$ represents hydrogen or $C_1$-$C_{10}$-alkyl, $C_6$-$C_{12}$-aryl or $C_7$-$C_{14}$-aralkyl,
- $R^4$ represents hydrogen or represents $C_1$-$C_{10}$-alkyl, $C_6$-$C_{12}$-aryl or $C_7$-$C_{14}$-aralkyl, or represents $C_1$-$C_{10}$-alkylsulphonyl, $C_6$-$C_{12}$-arylsulphonyl or $C_7$-$C_{14}$-aralkylsulphonyl, or represents an amino-protecting group, or represents a group of the formula in which
- $R^5$, $R^6$, $R^7$ and $R^8$ are identical or different and denote hydrogen, $C_1$-$C_{10}$-alkyl, $C_6$-$C_{12}$-aryl or $C_7$-$C_{14}$-aralkyl and
- X represents O, S, NH or $NCH_3$, and the salts thereof have now been found.

In the context of the abovementioned definition, amino-protecting group generally represents an amino-protecting group which is conventional in β-lactam chemistry. The following are vinyl, allyl, tert.butoxycarbonyl, benzyl, benzyloxycarbonyl, 2-nitrobenzyl, 4-nitrobenzyl, 2-nitrobenzyloxycarbonyl, 4-nitrobenzyloxycarbonyl, 4-methoxybenzyloxycarbonyl, formyl, benzoyl, acetyl, ethylcarbonyl, chloroacetyl, trichloroacetyl, trifluoroacetyl, methyloxycarbonyl, allyloxycarbonyl, trimethylsilyl, triethylsilyl, triphenylsilyl, tert.butyl-dimethylsilyl, methyldiphenylsilyl, 2,4-dimethoxybenzyl, 2,4-dimethoxybenzyloxycarbonyl, 4-methoxybenzyl, 4-(methoxymethyloxy)phenyl, bis-(4-methoxyphenyl)methyl, tert.butoxycarbonylmethyl, allyloxycarbonylmethyl, methoxymethyl, methylthiomethyl, methoxyethoxymethyl, [2-(trimethylsilyl)ethoxy]methyl or 2-(methylthiomethoxy)ethoxycarbonyl.

In the context of the abovementioned definition, hydroxyl-protecting group generally represents a hyroxyl-protecting group which is conventional in β-lactam chemistry. The following are trimethylsilyl, triethylsilyl, triisopropylsilyl, tert.butyl-dimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert.butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl.

In the context of the abovementioned definition, carboxyl-protecting group represents carboxyl-protecting group which is conventional in β-lactam chemistry. Groups which are easily cleaved off are, such as, for example: methyl, ethyl, tert.butyl, decyl, 2-chloroethyl, 2,2,2-trichloroethyl, cyanoethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert.butyl-dimethylsilyl, acetonyl, 1-phenoxyethyl or 2-methyl-2-propenyl.

If $R^2$ represents an ester radical which is easily cleaved off in vivo, this refers to pharmaceutically acceptable ester radicals which are easily hydrolyzed in vivo to form free carboxyl groups ($R^2$=H).

Such ester radicals are well known in the β-lactam field. In most cases, they improve the absorption properties of β-lactam compounds. In addition, the radical $R^2$ should be of a type such that it imparts pharmaceutically acceptable properties to a compound of the formula (I) and liberates pharmaceutically acceptable fragments on cleavage in vivo.

Examples of such groups are disclosed by DE-OS (German Published Specifications) 2,517,316. Preferred ester groups which can be cleaved off in vivo are those of the following formulae:

-continued $$-\underset{R^9}{\underset{|}{CH}}\underset{\underset{O}{|}}{=}\underset{\underset{\underset{O}{|}}{C}}{\underset{R^{10},}{|}} \quad -\underset{\underset{R^{12}}{|}}{\overset{\underset{R^{11}}{|}}{C}}-O-\overset{\overset{O}{\|}}{C}-R^{13} \text{ or}$$

$$-\underset{\underset{R^{12}}{|}}{\overset{\underset{R^{11}}{|}}{C}}-O-\overset{\overset{O^{\cdot}}{\|}}{C}-O-R^{13}$$

in which
  $R^9$ and $R^{10}$ are identical or different and represent hydrogen, phenyl or $C_1$-$C_4$-alkyl, preferably methyl,
  $R^{11}$ and $R^{12}$ are identical or different and represent hydrogen or $C_1$-$C_4$-alkyl, preferably methyl, and
  $R^{13}$ represents $C_1$-$C_6$-alkyl, preferably $C_1$-$C_4$-alkyl.

Preferred compounds of the general formula (I) are those in which
  $R^1$ represents hydrogen, or represents a hydroxyl-protecting group from the series comprising trimethylsilyl, triethylsilyl, triisopropylsilyl, tert.butyl-dimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert.butoxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyloxycarbonyl, methoxymethyl or methoxyethoxymethyl,
  $R^2$ represents hydrogen, or represents methyl, ethyl, tert.butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert.butyldimethylsilylethyl, or represents a radical of the formula

[structures]

—CH$_2$-OCO-C(CH$_3$)$_3$, —CH(CH$_3$)-OCOOC$_2$H$_5$ or —CH$_2$-OCOCH$_3$
  $R^3$ represents hydrogen or represents $C_1$-$C_6$-alkyl, or represents phenyl or benzyl,
  $R^4$ represents hydrogen or represents $C_1$-$C_6$-alkyl or represents phenyl or benzyl, or represents $C_1$-$C_4$-alkylsulphonyl, phenylsulphonyl or benzylsulphonyl, or represents an amino-protecting group from the series comprising allyl, tert.butoxycarbonyl, benzyl, benzyloxycarbonyl, 4-nitrobenzyl, 4-nitrobenzyloxycarbonyl, 4-methoxybenzyloxycarbonyl, formyl, acetyl, trichloroacetyl, 4-methoxyphenyl, 4-methoxybenzyl, 2,4-dimethoxybenzyl, 2-nitrobenzyloxycarbonyl, tert.butyl-dimethylsilyl, methyldiphenylsilyl, trimethylsilyl or trifluoroacetyl, or represents a group of the formula $$\overset{\overset{NR^5}{\|}}{\underset{}{\diagup}}R^6, \quad \overset{\overset{NR^5}{\|}}{\underset{}{\diagup}}NR^7R^8 \text{ or } \overset{\overset{O}{\|}}{\underset{}{\diagup}}NR^7R^8$$

in which $R^5$, $R^6$, $R^7$ and $R^8$ are identical or different, and denote hydrogen or $C_1$-$C_6$-alkyl, phenyl or benzyl and
  X represents O or S, or represents NH or NCH$_3$, and the salts thereof.

Particularly preferred compounds of the general formula (I) are those
in which
  $R^1$ represents hydrogen, or represents trimethylsilyl, triphenylsilyl, trimethylsilylethoxycarbonyl, tert.butyl-dimethylsilyl, 2-nitrobenzyloxycarbonyl, 4-nitrobenzyloxycarbonyl, allyloxycarbonyl or formyl,
  $R^2$ represents hydrogen, or represents methyl, ethyl, tert.butyl, 2,2,2-trichloroethyl, allyl, acetoxymethyl, 4-nitrobenzyl, 2-nitrobenzyl, 4-methoxybenzyl, benzyl or trimethylsilylethyl, or represents a radical of the formula

[structure: −H$_2$C−C(=)−CH$_3$ with O−C(=O)−O]

—CH(CH$_3$)-OCOOC$_2$H$_5$ or —CH$_2$-OCO-C(CH$_3$)$_3$
  $R^3$ represents hydrogen, $C_1$-$C_4$-alkyl or phenyl,
  $R^4$ represents hydrogen or represents $C_1$-$C_4$-alkyl, phenyl, tert.butyloxycarbonyl, benzyloxycarbonyl, acetyl, formyl or ethylcarbonyl, or represents a group of the formula $$\overset{\overset{NR^5}{\|}}{\underset{}{\diagup}}H, \quad \overset{\overset{NR^5}{\|}}{\underset{}{\diagup}}CH_3, \quad \overset{\overset{O}{\|}}{\underset{}{\diagup}}NH_2 \text{ or } \overset{\overset{NR^5}{\|}}{\underset{}{\diagup}}NR^7R^8$$

in which
  $R^5$, $R^7$ and $R^8$ are identical or different and denote hydrogen, methyl or phenyl,
and
  X represents S, NH or NCH$_3$,
and the salts thereof.

Besides the compounds according to the invention listed in the examples, the following compounds of the general formula (I), and the salts thereof, are particularly preferred:

| X | R⁴ | X | R⁴ |
|---|---|---|---|
| S | COCH₃ | O | COCH₃ |
| S | C(O)NH₂ | O | C(O)NH₂ |
| S | CHO | O | CHO |
| S | C(=NH)CH₃ | O | C(=NH)CH₃ |
| S | C(=NH)NH₂ | O | C(=NH)NH₂ |
| S | C(=NH)H | O | C(=NH)H |
| S | C(=NH)NHCH₃ | O | C(=NH)NHCH₃ |
| S | C(=NH)N(CH₃)₂ | O | C(=NH)N(CH₃)₂ |
| S | C(=NCH₃)N(CH₃)₂ | O | C(=NCH₃)N(CH₃)₂ |
| NH | COCH₃ | NCH₃ | COCH₃ |

-continued

| X | R⁴ | X | R⁴ |
|---|---|---|---|
| NH | C(O)NH₂ | NCH₃ | C(O)NH₂ |
| NH | CHO | NCH₃ | CHO |
| NH | C(=NH)CH₃ | NCH₃ | C(=NH)CH₃ |
| NH | C(=NH)NH₂ | NCH₃ | C(=NH)NH₂ |
| NH | C(=NH)H | NCH₃ | C(=NH)H |
| NH | C(=NH)NHCH₃ | NCH₃ | C(=NH)NHCH₃ |
| NH | C(=NH)N(CH₃)₂ | NCH₃ | C(=NH)N(CH₃)₂ |
| NH | C(=NCH₃)N(CH₃)₂ | NCH₃ | C(=NCH₃)N(CH₃)₂ |

The compounds, according to the invention, of the general formula (I) can exist as free acids, as esters, as intramolecular salts

[intramolecular salts structure shown]

or as nontoxic physiologically acceptable salts having a countercation

[salt having a countercation structure shown]

Countercations which are preferably mentioned are alkali metal cations or alkaline-earth metal cations, such as, for example, sodium ions, potassium ions, magnesium ions or calcium ions, or alumin ions or ammonium ions, and also nontoxic substituted ammonium ions derived from amines such as di(lower alkyl)amines, tri(-lower alkyl)amines, procaine, dibenzylamine, N,N'-dibenzylethylenediamine, N-benzyl-β-phenyl-ethylamine, N-methylmorpholine, N-methylmorpholine, 1-ephenamine, dihydroabiethylamine, N,N'-bis-dihydroabiethylethylenediamine, N-(lower alkyl)piperidine and other amines which can be used to form salts of β-lactam compounds.

The compounds according to the invention have several asymmetric carbon atoms and can thus exist in several stereochemical forms. The invention covers the mixtures of isomers and the individual stereoisomers. Preferred compounds of the formula (I) are those having the 5R, 6S, 8S configuration:

In addition, a process for the preparation of the benzazolylthio-carbapenem antibiotics, according to the invention, of the general formula (I), and the salts thereof, has been found which is characterized in that ketoesters of the general formula (II)

in which
R$^1$ has the meaning mentioned and
R$^{14}$ represents a carboxyl-protecting group or represents an ester radical which can be cleaved off in vivo and
thiols of the general formula (III)

in which
R$^3$, R$^4$ and X have the abovementioned meaning, are reacted with auxiliaries in inert solvents in the presence of bases,
protecting groups are cleaved off, if appropriate, and, if desired, the desired salts are prepared or the salts are converted into the free compounds.

If p-nitrobenzyl (2R,5R,6S)-3,7-dioxo-6-[(1R)-1-hydroxyethyl]-1-azabicyclo[3.2.0]heptane-2-carboxylate and 6-amino-2-mercapto-benzthiazole are used as starting materials, the process may be illustrated by the following equation:

-continued

Suitable solvents in this process are all organic solvents which are inert under the reaction conditions. These preferably include ethers, such as diethyl ether, dioxane, tetrahydrofuran, glycol dimethyl ether or butyl methyl ether, or hydrocarbons, such as benzene, toluene, xylene, hexane, or mineral oil fractions, or halogenated hydrocarbons, such as dichloromethane, trichloromethane, tetrachloromethane, 1,1,2-trichloroethane, dichloroethylene or trichloroethylene, chlorobenzene or dichlorobenzene, or amides, such as dimethylformamide, dimethylacetamide, hexamethylphosphoric triamide, 1,3-dimethyl-2-imidazolidinone (DMI), N,N'-dimethyl-propyleneurea (DMPU), or acetone, ethyl acetate, sulpholane, dimethyl sulphoxide or acetonitrile. It is likewise possible to employ mixtures of the solvents mentioned.

Suitable bases are the conventional organic bases. These preferably include trialkylamines, such as, for example, trimethylamine, triethylamine, tripropylamine, tributylamine or ethyldiisopropylamine, or tertiary organic bases, such as pyridine, dimethylaminopyridine, picoline, lutidine, N-methylmorpholine, N-methylpiperidine, 1,5-diazabicyclo[5.4.0]undec-5-ene (DBU) or 1,5-diazabicyclo[4.3.0]non-3-ene (DBN).

The auxiliaries employed are generally substances which convert the ketoesters of the general formula (II) into compounds of the general formula (IV)

(IV)

in which
R$^1$ and R$^{14}$ have the abovementioned meaning, and
Z represents a leaving group from the series comprising

—O—P(OC$_6$H$_5$)$_2$, —OSO$_2$CF$_3$, —OSO$_2$—⟨⟩—CH$_3$

∥
O

—OSO$_2$—⟨⟩—Br, preferably —O—P(OC$_6$H$_5$)$_2$
∥
O

These preferably include acid halides or acid anhydrides of 4-toluenesulphonic acid, 4-bromophenylsulphonic acid, trifluoromethanesulphonic acid, or diphenyl chlorophosphate. Diphenyl chlorophosphate is particularly preferably used.

The reaction can be carried out in one step without isolation of the intermediates. However, it has proven favo to isolate the intermediates of the general formula (IV).

The process is preferably carried out by reacting the intermediates with the appropriate thiol in a suitable solvent, if appropriate in the presence of bases.

It is likewise possible to employ the thiol (III) in the form of its salts or to prepare the corresponding thiolate by adding base to the reaction mixture.

The base is generally employed in an amount of 1 to 3 mol preferably 1 to 1.5 mol relative to 1 mol of the ketoester. The thiol is generally employed in an amount of 1 to 4 mol preferably 1 to 2 mol relative to 1 mole of the ketoester. If the thiolate is generated from the thiol in the reaction solution, further base is employed in amounts of 1 to 5 mol preferably 1 to 2 mol relative to 1 mol of thiol.

The reaction is generally carried out in a temperature range from −80° C. to +60° C., preferably from −50° C. to +40° C. The reaction is generally carried out at atmospheric pressure. However, it is likewise possible to carry out the reaction at subatmospheric pressure or superatmospheric pressure.

The thiols of the general formula (III) employed as starting materials are known or can be prepared by known methods [G. Bloeckingen et al., Czechoslovakian Patent Application 168,746/15.4.1977; CA 88, 37786(1978); V. Sutoris et al., Chem. Zvest. 27, 698(1973); CA 80, 95814(1974); J. Roy et al. Indian J. Chem., Sect B, (14B(7), 536(1976)).

The ketoesters of the general formula (II) employed as starting materials are known or can be prepared by known methods [T. N. Salzmann et al., J. Am. Chem. Soc. 102, 6163 (1980)].

Compared to conventional carbapenem antibiotics, such as, for example, thienamycin or imipenem, the compounds according to the invention surprisingly have an improved antibacterial activity, particularly against numerous Staphylococci and Enterococci. In addition, the carbapenems, according to the invention, of the formula (I) exibit metabolic stability to the enzyme dehydropeptidase (I) (DHP I) and are thus superior, in respect of compatibility, to other compounds of this class of substances.

These valuable properties permit their use as chemotherapeutic active compounds in medicine and as compounds for preserving inorganic and organic materials, in particular organic materials of all kinds, for example polymers, lubricants, paints, fib leather, paper and timber, foodstuffs and water.

The compounds according to the invention are active against a very broad spectrum of microorganisms. They can be used to combat Gram-negative and Gram-positive bacteria and bacteria-like microorganisms and to prevent, ameliorate and/or heal disorders caused by these pathogens.

The compounds according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systemic disorders caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative bacilli, such as Enterobacteriaceae, for example *Escherichia coli, Haemophilus influenzae,* Citrobacter (*Citrob. freundii* and *Citrob. divernis*), Salmonella and Shigella; furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the Acinetobacter genus. In addition, the antibacterial spectrum covers strictly anaerobic bacteria, such as, for example, *Bacteroides fragilis,* representatives of the Peptococcus genus, Peptostreptococcus and the Clostridium genus; furthermore Mycoplasma (*M. pneumoniae, M. hominis* and *M. urealyticum*) and Mycobacteria, for example I Mycobacterium tuberculosis.

The above list of pathogens is purely illustrative and is in no way to be interpreted as restrictive. The following may be mentioned as examples of illnesses which can be caused by the pathogens mentioned or by mixed infections and can be prevented, ameliorated and/or heated by the compounds according to the invention:

Infectious diseases in humans, such as, for example, otitis, pharyngitis, pneumonia, peritonitis, pyelonephritis, cystitis, endocarditis, systemic infections, bronchitis (acute and chronic), septic infections, disorders of the upper respiratory tracts, diffuse panbronchiolitis, pulmonary emphysema, dysentery, enteritis, liver abscesses, urethritis, prostatitis, epididymitis, gastro-intestinal infections, bone and joint infections, cystic fibrosis, skin infections, postoperative wound infections, abscesses, phlegmon, wound infections, infected burns, burn wounds, oral infections, infections after dental operations, osteomyelitis, septic arthritis, cholecystitis, peritonitis with appendicitis, cholangitis, intraabdominal abcesses, pancreatitis, sinusitis, mastoiditis, mastitis, tonsillitis, typhoid, meningitis and infections of the nervous system, salpingitis, endometritis, genitial infections, pelveoperitonitis and eye infections.

Apart from in humans, bacterial infections can also be treated in other species. Examples which may be mentioned are:

Pig: coli-diarrhoea, enterotoxaemia, sepsis, dysentery, salmonellosis, metritis-mastitis-agalactiae syndrome and mastitis;

Ruminants (cattle, sheep and goat): diarrhoea, sepsis, bronchopneumonia, salmonellosis, pasteurellosis, mycoplasmosis and genital infections;

Horse: bronchopneumonia, joint-ill, puerperal and postpuerperal infections, and salmonellosis;

Dog and cat: bronchopneumonia, diarrhoea, dermatitis, otitis, urinary tract infections and prostatitis;

Poultry (chicken, turkey, quail, dove, cage birds and others): mycoplasmosis, *E. coli* infections, chronic respiratory tract disorders, salmonellosis, pasteurellosis and psittacosis.

Bacterial infections in the breeding and keeping of productive and ornamental fish can likewise be treated, the antibacterial spectrum extending beyond the previously mentioned pathogens to further pathogens, such as, for example, Pasteurella, Brucella, Campylobacter, Listeria, Erysipelothrix, Corynebacteria, Borellia, Treponema, Nocardia, Rickettsia, Yersinia.

The present invention includes pharmaceutical preparations which, in addition to non-toxic, inert pharmaceutically suitable excipients, contain one or more compounds according to the invention or which comprise one or more active compounds according to the invention, and processes for the production of these preparations.

The present invention also includes pharmaceutical preparations in dosage units. This means that the preparation are in the form of individual parts, for example tablets, dragees, capsules, pills, suppositories and amp of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

Non-toxic, inert pharmaceutically suitable excipients are taken to mean solid, semisolid or liquid diluents, fillers and formulation auxiliaries of all kinds.

Tablets, dragees, capsules, pills, granules, suppositories, solution, suspensions and emulsions, pastes, ointments, gels, creams, lotions, powders and sprays may be mentioned as preferred pharmaceutical preparations.

Tablets, dragees, capsules, pills and granules can contain the active compound or compounds together with the customary excipients such as (a) fillers and extenders, for example starches, lactose, sucrose, glucose, mannitol and silica, (b) binders, for example carboxymethylcellulose, alginates, gelatin and polyvinylprrolidone, (c) humectants, for example glycerine, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract optionally in a delayed manner, examples of embedding compositions which can be used being polymer substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxides or mixtures of these substances.

Powders and sprays can contain the customary excipients in addition to the active compound or compounds, for example lactose, talc, silica, alumin hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and polyoxyethylene sorbitan esters, microcrystalline cellulose, alumin metahydroxide, bentonite, agar-agar and tragacanth, or mixtures of these substances.

The formulation forms mentioned can also contain dyestuffs, preservatives and additives which improve the odour and flavour, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutically active compounds in addition to the compounds according to the invention.

The abovementioned pharmaceutical preparations are manufactured in the usual manner according to known methods, for example by mixing the active compound or the active compounds with the excipient or excipients.

In humans and animals, the preparations mentioned can be administered either orally, rectally, parenterally (intravenously, intramuscularly or subcutaneously), intracisternally, intravaginally, intraperitoneally, locally (powder, ointment or drops) and for therapy of infections in cavities and body cavities. Suitable preparations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy. In the case of animals, intake can also be effected in suitable formulations via the feed or drinking water. Furthermore, gels, oral powders, dusting powders, tablets, retard tablets, premixes, concentrates, granules, pellets, tablets, boli, capsules, aerosols, sprays and inhalants may be used in humans and animals. Furthermore, the compounds according to the invention can be incorporated into other excipient materials, such as, for example, plastics, (plastic chains for local therapy), collagen or bone cement.

In general, it has proved advantageous, both in human medicine and veterinary medicine, to administer the active compound or compounds in total amounts of about 0.5 to about 500, preferably 5 to 100 mg/kg of body weight every 24 hours, if appropriate in the form of several individual administrations, in order to achieve the desired results. An individual administration contains the active compound or compounds according to the invention preferably in amounts of about 1 to about 80, particularly 3 to 30, mg/kg of body weight. However, it may be necessary to deviate from the dosages mentioned and in particular to do so as a function of the nature and the body weight of the subject to be treated, the nature and severity of the disorder, the nature of the preparation and of the administration of the medicament, and the time or interval over which the administration takes place.

Thus, it may suffice, in some cases, to manage with less than the abovementioned amount of active compound, whilst in other cases the abovementioned amount of active compound must be exceeded. The particular optimum dosage required and the type of administration of the active compounds can easily be decided by anyone skilled in the art, on the basis of his expert knowledge.

The new compounds can be administered, in the usual concentrations and preparations, together with the feedstuff or the feedstuff preparations, or with the drinking water. This permits infection by Gram-negative or Gram-positive bacteria to be prevented, ameliorated and/or healed, and thereby allows promotion of growth and improved utilization of the feedstuff to be achieved.

The MIC values of some of the compounds according to the invention are given in the following table, comparing with imipanem.

Antibacterial action:

The agar solution method was used for determining the antibacterial action, an Iso-sensitest agar being used and the minimum inhibitory concentration (MIC) of the sample being expressed in $\mu g/ml$ of the nutrient medium (Table).

| Pathogen | Compound from Ex. 5 | Compound from Ex. 6 | imipenem |
|---|---|---|---|
| *Proteus mir.* 1235 | 1 | 0.5 | 4 |
| *Staph. aur.* 1756 | 4 | 1 | 16 |
| *Staph. aur.* 133 | ≦0.0625 | ≦0.0625 | ≦0.0625 |
| *Staph. aur.* 25022 | ≦0.0625 | ≦0.0625 | ≦0.0625 |
| *Staph. e.* 25 185 | 0.125 | ≦0.0625 | ≦0.0625 |
| *Strept. faec.* 27101 | 2 | 0.5 | 4 |
| *Strept. faec.* 113 | 2 | 1 | 0.5–1 |
| *Enterococc.* 9790 | 2 | 0.5 | 4 |
| *Enterococc.* 27158 | 1 | 1 | 0.5–1 |

PREPARATION EXAMPLES

Example 1 p-Nitrobenzyl (5R,6S)-3-diphenylphosphonyloxy-6-[(1R)-1-hydroxyethyl]-7-oxo-1-azabicyclo[3.2.0]hept-2-ene-2-carboxylate

*Structure diagram: p-nitrobenzyl (5R,6S)-3-diphenylphosphonyloxy-6-[(1R)-1-hydroxyethyl]-7-oxo-1-azabicyclo[3.2.0]hept-2-ene-2-carboxylate*

1.82 ml (10.5 mmol) of N,N-diisopropylethylamine and 2.18 ml (10.5 mmol) of diphenyl chlorophosphate were simultaneously added dropwise, within 5 minutes, to a solution, cooled to 0° C., of 3.48 g (10.0 mmol) of p-nitrobenzyl (2R,5R,6S)-3,7-dioxo-6[(1R)-1-hydroxyethyl]-1-azabicyclo[3.2.0]heptane-2-carboxylate [T. N. Salzmann et al., J. Am. Chem. Soc. 102, 6163 (1980)] in 40 ml of anhydrous acetonitrile. The mixture was stirred at 0° C. for 30 minutes and then poured into a mixture of cold NaHCO$_3$ solution and ethyl acetate. The mixture was extracted with ethyl acetate, and the organic extracts were washed with NaHCO$_3$ solution and dried over MgSO$_4$. After evaporation of the solvent in vacuo and drying of the residue in a high vacuum, the title compound was obtained as a pale foam, which was further reacted directly.

$R_f$: 0.45 (toluene:ethyl acetate 3:7)

IR (KBr): 3450, 1782, 1729, 1643, 1590, 1526, 1490, 1350 cm$^{-1}$ $^1$H NMR (200 MHz, CDCl$_3$): δ=1.34 (d, j=6.5 Hz, 3H, CH$_3$CHOH), 3.25 (m, 3H, H-4, H-4', H-6), 4.25 (m, 2H, H-5, CH$_3$CHOH), 5.25 and 5.41 (AB, J=13 Hz, 2H, COOCH$_2$), 7.2–7.5 (m, 10H, Ph), 7.59 and 8.17 (AB, J=8.5 Hz, 4H, p—NO$_2$—C$_6$H$_4$).

EXAMPLE 2 p-Nitrobenzyl (5R,6S)-3-(6-amino-2-benzthiazolylthio)-6-[(1R)-1-hydroxethyl]-7-oxo-1-azabicyclo[3.2.0-]hept-2-ene-2-carboxylate

*Structure diagram*

0.55 ml (3.15 mmol) of N,N-diisopropylethylamine was added dropwise to a solution, cooled to −40° C., of 1.74 g (3.0 mmol) of p-nitrobenzyl (5R,6S)-3-diphenylphosphonyloxy-6-[(1R)-1-hydroxyethyl]-7-oxo-1-azabicyclo[3.2.0]hept-2-ene-2-carboxylate in 6 ml of anhydrous dimethylformamide, and 0.57 g (3.15 mmol) of 6-amino-2-mercaptobenzthiazole was subsequently added. The suspension was allowed to warm to 0° C. within 2 hours and was then stirred at 0° C. for 42 hours, a clear solution being produced. For work-up, the solution was poured into a mixture of ice, NaHCO$_3$ solution and ethyl acetate and extracted with ethyl acetate, and the organic extracts were washed with cold NaHCO$_3$ solution (2×) and dried over MgSO$_4$. After evaporation of the solvent in vacuo and chromatography of the residue on 45 g of silica gel (toluene:ethyl acetate 2:3), 465 mg (30% of theory) of the title compound were obtained as pale crystals.

Melting point: 190° C. (decomp.)

$R_f$: 0.12 (toluene:ethyl acetate 1:1)

IR (KBr): 1766, 1691, 1628, 1602, 1575, 1518, 1338 cm$^{-1}$ $^1$H NMR (200 MHz, DMSO): δ=1.06 (d, J=6.5 Hz, 3H, CH$_3$CHOH), 2.94 and 3.15 (ABd, J=18.5 Hz, 10 Hz, 2H, H-4), 3.45 (dd, J=6 Hz, 2.5 Hz, 1H, H-6), 3.94 (dq, J=6.5 Hz, 6 Hz, 1H, CH$_3$CHOH), 4.17 (dt, 10 Hz, 2.5 Hz, 1H, H-5), 5.04 (d, J=6 Hz, 1H, OH), 5.40 and 5.54 (AB, J=14.5 Hz, 2H, CQOCH$_2$), 5.72 (bs, 2H, NH$_2$), 6.78 (dd, J=9 Hz, 2 Hz, 1H, H-5'), 7.10 (d, J=2 Hz, 1H, H-7'), 7.75 (d, J=9 Hz, 1H, H-4'), 7.78 and 8.31 (AB, J=9 Hz, 4H, p—NO$_2$—C$_6$H$_4$).

EXAMPLE 3 p-Nitrobenzyl (5R,6S)-3-(6-formylamino-2-benzthiazolylthio)-6-[(1R)-1-hydroxyethyl]-7-oxo-1-azabicyclo[3.2.0]-hept-2-ene-2-carboxylate

*Structure diagram*

Process variant A:

As described for Example 2, 376 mg (35% of theory) of the title compound were obtained as colo crystals from 1.08 g (2.0 mmol) of p-ntirobenzyl (5R,6S)-3-diphenylphosphonyloxy-6-[(1R)-1-hydroxyethyl]-7-oxo-1-azabicyclo[3.2.0]hept-2-ene-2-carboxylate and 0.38 g (2.1 mmol) of 6-formylamino-2-mercapto-benzthiazole after 42 hours at 0° C. (clear solution after 45 minutes) and chromatography of the crude product on 77 g of silica gel (toluene:ethyl acetate 1:4).

Melting point: 174° C. (decomp.)

$R_f$: 0.17 (toluene:ethyl acetate 1:4)

IR (KBr) 3442, 1783, 1688, 1645, 1607, 1557, 1526, 1338 cm$^{-1}$ $^1$H NMR (200 MHz, DMSO): δ=1.08 (d, J=6.5 Hz, 3H, CH$_3$CHOH), 3.15 and 3.38 (m, 2H, H-4), 3.48 (dd, J=6 Hz, 3 Hz, 1H, H-6), 3.95 (dq, J=6.5 Hz, 6 Hz, 1H, CH$_3$CHOH), 4.21 (dt, J=10 Hz, 3 Hz, 1H, H-5), 5.07 (d, J=5 Hz, 1H, OH) 5.41 and 5.56 (AB, J=14 Hz, 2H, COOCH$_2$), 7.17 (dd, J=9.5 Hz, 1.5 Hz, 1H, H-5'), 7.78 and 8.30 (AB, J=9 Hz, 4H, p—NO$_2$—C$_6$H$_4$), 8.06 (d, J=9.5 Hz, 1H, H-4'), 8.41 (bs, 1H, NHCHO), 8.58 (d, J=1.5 Hz, 1H, H-7'), 10.60 (bs, 1H, NHCHO).

Process variant B:

0.3 ml (1.73 mmol-1.05 equivalents) of ethyldiisopropylamine and 0.36 ml (1.73 mmol) of diphenyl chlorophosphate were added simultaneously within 10 minutes to a solution, cooled to 0° C., of 571 mg (1.64 mmol) of p-nitrobenzyl (2R,5R,6S)-3,7-dioxo-6-[(1R)-1-hydroxyethyl]-1-azabicyclo[3.2.0]heptane-2-carboxylate [T. N. Salzmann et al., J. Am. Chem. Soc. 102, 6163 (1980)] in 8 ml of anhydrous acetonitrile. The mixture was then stirred for 15 minutes at 0° C. and cooled to −40° C., and 0.32 ml (1.81 mmol-1.1 equivalents) of ethyl diisopropylamine and 323 mg (1.81 mmol) of 6-formylamino-2-mercapto-benzthiazole were added successively. The reaction mixture was allowed to warm to 0° C. and, when complete, was stirred into a cold mixture of NaHCO$_3$ solution and ethyl acetate. The mixture was extracted with ethyl acetate, washed with NaCl solution and water and dried over MgSO$_4$. After evaporation of the solvent in vacuo and chromatography of the residue on 100 g of silica gel, 152 mg (17% of theory) of the title compound were obtained. The physical values were identical to the substance obtained by process variant A.

EXAMPLE 4 p-Nitrobenzyl (5R,6S)-3-(6-amino-2-benzimidazolylthio)-6-[(1R)-1-hydroxyethyl]-7-oxo-1-azabicyclo[3.2.0-]hept-2-ene-2-carboxylate As described for Example 2, 465 mg (9.5% of theory) of the title compound were obtained as colo crystals from 5.80 g (10.0 mmol) of p-nitrobenzyl (5R,6S)-3-diphenylphosphonyloxy-6-[(1R)-1-hydroxyethyl]-7-oxo-1-azabicyclo[3.2.0]hept-2-ene-2-carboxylate and 1.74 g (10.5 mmol) of 6-amino-2-mercapto-benzimidazole after 67 hours at 0° C. and chromatography of the crude product on 600 g of silica gel (ethyl acetate:acetonitrile 85:15).

Melting point: 168° C. (decomp.)

R$_f$=0.27 (ethyl acetate:acetonitrile 4:1)

IR (KBr) 1756, 1740, 1723, 1661, 1629, 1568, 1520, 1480, 1349 cm$^{-1}$ $^1$H NMR (200 MHz, DMSO): δ=1.12 (d, J=6.5 Hz, 3H, CH$_3$CHOH), 2.76 (m, 2H, H-4), 2.90 (dd, J=7 Hz, 2 Hz, 1H, H-6), 3.88 (dq, J=7 Hz, 6.5 Hz, 1H, CH$_3$CHOH), 4.00 (dt, J=6.5 Hz, 2 Hz, 1H, H-5), 4.14 (bs, 2H, NH$_2$), 4.95 (d, J=4 Hz, 1H, OH), 5.19 (s, 2H, COOCH$_2$), 7.02 (d, J=9 Hz, 1H, H-4'), 7.14 (dd, J=9 Hz, 1.5 Hz, 1H, H-5'), 7.64 and 8.12 (AB, J=9.5 Hz, 4H, p-NO$_2$-C$_6$H$_4$), 7.64 (d, J=1.5 Hz, 1H, H-7'), 10.10 (bs, 1H, NH).

EXAMPLE 5

(5R,6S)-3-(Amino-2-benzthiazolylthio)-6-[(1R)-1-hydroxyethyl]-7-oxo-1-azabicyclo[3.2.0]hept-2-ene-2-carboxylic acid A solution of 450 mg (0.87 mmol) of p-nitrobenzyl (5R,6S)-3-(6-amino-2-benzthiazolylthio)-6-[(1R)-1-hydroxyethyl]-7-oxo-1-azabicyclo[3.2.0]hept-2-ene-2-carboxylate in 12.5 ml of a mixture comprising tetrahydrofuran and 0.1M phosphate buffer pH 7 (1:1) was hydrogenated for 1.5 hours in the presence of 450 mg of palladium on charcoal (10%). The catalyst was then separated off by filtration through kieselguhr, the tetrahydrofuran was removed in vacuo, and the solution remaining was adjusted to pH 7. The aqueous solution was extracted twice with ethyl acetate, concentrated to about 10 ml in vacuo, and transferred to a column with 120 ml of Diaion HP 20. The column was eluted with water containing an increasing proportion of acetonitrile. The fractions containing the product were collected, filtered through a 0.2μ filter and freeze-dried. 253 mg (73% of theory) of the title compound were obtained as a colo lyophili ate. R$_f$=0.26 (acetonitrile:water=9:1) in a purity of 97% (HPLC).

IR (KBr) 3420, 1763, 1601, 1477, 1403 cm$^{-1}$ $^1$H NMR (200 MHz, D$_2$O): δ=1.19 (d, J=7 Hz, 3H, CH$_3$CHOH), 2.86 (m, 2H, H-4), 3.31 (dd, J=6 Hz, 2.5 Hz, 1H, H-6), 4.13 (dt, J=7 Hz, 2.5 Hz, H-5), 4.18 (dq, J=7 Hz, 7 Hz, CH$_3$CHOH), together 2H), 7.05 (dd, J=9 Hz, 1.5 Hz, 1H, H-5'), 7.25 (d, J=1.5 Hz, 1H, H-7'), 7.78 (d, J=9 Hz, 1H, H-4').

EXAMPLE 6

Sodium (5R,6S)-3-(6-formylamino-2-benzthiazolylthio)-6-[(1R)-1-hydroxyethyl]-7-oxo-1-azabicyclo[3.2.0-]hept-2-ene-2-carboxylate As described for Example 5, 1.95 g (90% of theory) of the title compound were obtained as a colo lyophili ate from 2.73 g (5.05 mmol) of p-nitrobenzyl (5R,6S)-3-(6-formylamino-2-benzthiazolylthio)-6-[(1R)-1-hydroxyethyl]-7-oxo-1-azabicyclo[3.2.0]hept-2-ene-2-carboxylate.

R$_f$=0.3 (acetonitrile:H$_2$O 9:1), in a purity of 96% (HPLC).

IR (KBr) 3403, 1764, 1684, 1601, 1402 cm$^{-1}$ $^1$H NMR (200 MHz, D$_2$O): δ=1.09 (d, J=7 Hz, 3H, CH$_3$CHOH), 2.80 and 2.85 (bs, 2H, H-4), 3.28 (m, 1H, H-5), 4.06 (m, 2H, H-5, CH$_3$CHOH), 7.30 (d, J=9 Hz, 1H, H-5'), 7.63 (d, J=9 Hz, 1H, H-4'), 7.94 (s, 1H, H-7'), 8.20 (s, 1H, CHO).

EXAMPLE 7

(5R,6S)-3-(6-Amino-2-benzimidazolylthio)-6-[(1R)-1-hydroxyethyl]-7-oxo-1-azabicyclo[3.2.0]hept-2-ene-2-carboxylic acid As described for Example 5, 384 mg (97% of theory) of the title compound were obtained as a colo lyophili ate from 550 mg (1.1 mmol) of p-nitrobenzyl (5R,6S)-3-(6-amino-2-benzimidazolylthio)-6-[(1R)-1-hydroxyethyl]-7-oxo-1-azabicyclo[3.2.0]hept-2-ene-2-carboxylate.

R$_f$=0.20 (acetonitrile:H$_2$O 9:1), in a purity of 98% (HPLC).

IR (KBr) 3440, 1760, 1659, 1627, 1477, 1385 cm$^{-1}$ $^1$H NMR (300 MHz, D$_2$O): δ=1.25 (d, J=6.5 Hz, 2H, C$\underline{H_3}$CHOH), 2.87 (dd, J=15 Hz, 7.5 Hz, 1H, H-4), 2.97 (dd, J=15 Hz, 8 Hz, 1H, H-4), 3.18 (dd, J=6.5 Hz, 2.5 Hz, 1H, H-6), 4.2 (m, 2H, CH$_3$C$\underline{H}$OH, H-5), 7.11 (dd, J=9 Hz, 1 Hz, 1H, H-5′), 7.20 (d, J=9 Hz, 1H, H-4′), 7.37 (d, J=1 Hz, 1H, H-7′).

We claim:

1. A benzazolylthiocarbapenem of the formula

[Structure shown]

in which

R$^1$ represents hydrogen, trimethylsilyl, triethylsilyl, triisopropylsilyl, tert.butyl-dimethylsilyl, triphenylsilyl, trimethylsilylethoxy-carbonyl, benzyl, benzyloxycarbonyl, 2-nitrobenzyl, 4-nitrobenzyl, 2-nitrobenzyloxycarbonyl, 4-nitrobenzyloxycarbonyl, tert.butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl, R$^2$ represents hydrogen, methyl, ethyl, tert.butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert.butyldimethylsilylethyl; or a radical from the group consisting of

[Structures shown]

in which

R$^9$ and R$^{10}$ are identical or different and represent hydrogen, phenyl or C$_1$–C$_4$-alkyl, R$^{11}$ and R$^{12}$ are identical or different and represent hydrogen or C$_1$–C$_4$-alkyl and R$^{13}$ represents C$_1$–C$_6$-alkyl, R$^3$ represents hydrogen or C$_1$–C$_{10}$-alkyl, C$_6$–C$_{12}$-aryl or C$_7$–C$_{14}$-aralkyl, R$^4$ represents hydrogen or represents C$_1$–C$_{10}$-alkyl, C$_6$–C$_{12}$-aryl or C$_7$–C$_{14}$ aralkyl, or represents C$_1$–C$_{10}$-alkylsulphonyl, C$_6$–C$_{12}$-arylsulphonyl or C$_7$–C$_{14}$-aralkylsulphonyl, or represents vinyl, allyl, tert.butoxycarbonyl, benzyl, benzyloxycarbonyl, 2-nitrobenzyl, 4-nitrobenzyl, 2-nitrobenzyloxycarbonyl, 4-nitrobenzyloxycarbonyl, 4-methoxybenzyloxycarbonyl, formyl, benzoyl, acetyl, ethylcarbonyl, chloroacetyl, trichloroacetyl, trifluoroacetyl, methyloxycarbonyl, allyloxycarbonyl, trimethylsilyl, triethylsilyl, triphenylsilyl, tert.butyldimethylsilyl, methyldiphenylsilyl, 2,4-dimethoxybenzyl, 2,4-dimethoxybenzyloxycarbonyl, 4-methoxybenzyl, 4-(methoxymethyloxy)phenyl, bis-(4-methoxyphenyl)-methyl, tert.butoxycarbonylmethyl, allyloxycarbonylmethyl, methoxymethyl, methylthiomethyl, methoxyethoxymethyl, [2-(trimethylsilyl)ethoxy]methyl or 2-(methylthiomethoxy)ethoxycarbonyl; or represents a group of the formula

[Structures shown]

in which

R$^5$, R$^6$ and R$^8$ are identical or different and denote hydrogen, C$_1$–C$_{10}$-alkyl, C$_6$–C$_{12}$-aryl or C$_7$–C$_{14}$-aralkyl, and X represents O, S, NH or NCH$_3$, or a salt thereof.

2. A compound or salt according to claim 1, in which

R$^1$ represents hydrogen, or represents a hydroxyl-protecting group from the series comprising trimethylsilyl, triethylsilyl, triisopropylsilyl, tert.butyl-dimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert.butoxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyloxycarbonyl, methoxymethyl or methoxyethoxymethyl, R$^2$ represents hydrogen, or represents methyl, ethyl, tert.butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert.butyldimethylsilylethyl, or represents a radical of the formula

[Structures shown]

-continued $$-H_2C\underset{\underset{O}{\overset{\|}{C}}}{\overset{}{\underset{O}{\bigg|}}}\overset{}{\underset{O}{\bigg|}}CH_3$$

—CH$_2$—OCO—C(CH$_3$)$_3$,  —CH(CH$_3$)—OCOOC$_2$H$_5$ or —CH$_2$—OCOCH$_3$,

R$^3$ represents hydrogen or represents C$_1$–C$_6$-alkyl, or represents phenyl or benzyl, R$^4$ represents hydrogen or represents C$_1$–C$_6$-alkyl or represents phenyl or benzyl, or represents C$_1$–C$_4$-alkylsulphonyl, phenylsulphonyl or benzylsulphonyl, or represents an amino-protecting group from the series comprising allyl, tert.butoxycarbonyl, benzyl, benzyloxycarbonyl, 4-nitrobenzyl, 4-nitrobenzyloxycarbonyl, 4-methoxybenzyloxycarbonyl, formyl, acetyl, trichloroacetyl, 4-methoxyphenyl, 4-methoxybenzyl, 2,4-dimethoxybenzyl, 2-nitrobenzyloxycarbonyl, tert.butyl-dimethylsilyl, methyldiphenylsilyl, trimethylsilyl or trifluoroacetyl, or represents a group of the formula $$\overset{NR^5}{\underset{R^6}{\|}}, \quad \overset{NR^5}{\underset{NR^7R^8}{\|}} \text{ or } \overset{O}{\underset{NR^7R^8}{\|}}$$

in which

R$^5$, R$^6$, R$^7$ and R$^8$ are identical or different, and denote hydrogen or C$_1$–C$_6$-alkyl, phenyl or benzyl, and X represents O or S, or represents NH or NCH$_3$.

3. A compound or salt according to claim 1, in which

R$^1$ represents hydrogen, or represents trimethylsilyl, triphenylsilyl, trimethylsilylethoxycarbonyl, tert.butyl-dimethylsilyl, 2-nitrobenzyloxycarbonyl, 4-nitrobenzyloxycarbonyl, allyloxycarbonyl or formyl, R$^2$ represents hydrogen, or represents methyl, ethyl, tert.butyl, 2,2,2-trichloroethyl, allyl, acetoxymethyl, 4-nitrobenzyl, 2-nitrobenzyl, 4-methoxybenzyl, benzyl or trimethylsilylethyl, or represents a radical of the formula $$-H_2C\underset{\underset{O}{\overset{\|}{C}}}{\overset{}{\underset{O}{\bigg|}}}\overset{}{\underset{O}{\bigg|}}CH_3$$

—CH(CH$_3$)—OCOOC$_2$H$_5$  or  —CH$_2$—OCO—C(CH$_3$)$_3$,

R$^3$ represents hydrogen, C$_1$–C$_4$-alkyl or phenyl,

R$^4$ represents hydrogen or represents C$_1$–C$_4$-alkyl, phenyl, tert.butyloxycarbonyl, benzyloxycarbonyl, acetyl, formyl or ethylcarbonyl, or represents a group of the formula $$\overset{NR^5}{\underset{H}{\|}}, \quad \overset{NR^5}{\underset{CH_3}{\|}}, \quad \overset{O}{\underset{NH_2}{\|}} \text{ or } \overset{NR^5}{\underset{NR^7R^8}{\|}}$$

in which

R$^5$, R$^7$ and R$^8$ are identical or different and denote hydrogen, methyl or phenyl, and X represents S, NH or NCH$_3$.

4. A compound according to claim 1 wherein such compound is (5R,6S)-3-(6-amino-2-benzthiazolylthio)-6-[(1R)-1-hydroxyethyl]-7-oxo-1-azabicyclo[3.2.0]hept-2-ene-2-carboxylic acid of the formula 5. A compound according to claim 1 wherein such compound is (5R,6S)-3-(6-formylamino-2-benzthiazolyl-thio)-6-[(1R)-1-hydroxyethyl]-7-oxo-1-azabicyclo[3.2.0]-hept-2-ene-2-carboxylic acid of the formula or a salt thereof.

6. A compound according to claim 1 wherein such compound is (5R,6S)-3-(6-amino-2-benzimidazolylthio)-6-[(1R)-1-hydroxyethyl]-7-oxo-1-azabicyclo[3.2.0-]hept-2-ene-2-carboxylic acid of the formula 7. An antibiotically active composition comprising an antibiotically effective amount of a compound or salt according to claim 1 and a diluent.

8. A unit dose of a composition according to claim 7 in the form of a tablet, pill or capsule.

9. A method of combating infection which comprises administering to a patient in need thereof an antibiotically effective amount of a compound or salt according to claim 1.

10. The method according to claim 9, wherein such compound is (5R,6S)-3-(6-amino-2-benzthiazolylthio)-6-[(1R)-1-hydroxyethyl]-7-oxo-1-azabicyclo[3.2.0]hept-2-ene-2-carboxylic acid, (5R,6S)-3-(6-formylamino-2-benzthiazolyl-thio)-3-[(1R)-1-hydroxyethyl]-7-oxo-1-azabicyclo[3.2.0]-hept-2-ene-2-carboxylic acid or a salt thereof, or (5R,6S)-3-(6-amino-2-benzimidazolylthio)-6-[)1R)-1-hydroxyethyl]-7-oxo-1-azabicyclo[3.2.0]hept-2-ene-2-carboxylic acid.

* * * * *

UNITED STATES PATENT AND TRADEMARK OFFICE
CERTIFICATE OF CORRECTION

PATENT NO. : 4,840,946

DATED : June 20, 1989

INVENTOR(S) : Habich et al.

It is certified that error appears in the above-identified patent and that said Letters Patent is hereby corrected as shown below:

Title Page [54] Invention: Delete " BENZAZOLYTHIO " and substitute -- BENZAZOLYLTHIO --

Title Page ABSTRACT: Delete "[structure]" and substitute -- [structure] --

Col. 1, line 1    Delete " BENZAZOLYTHIO " and substitute -- BENZAZOLYLTHIO --

Col. 1, line 32   Delete "[structure]" and substitute -- [structure] --

Col. 5, line 6    Delete "[structure]" and substitute -- [structure] --

Col. 6, line 6    Delete "[structure]" and substitute -- [structure] --

Col. 6, line 43   Delete "[structure]" and substitute -- [structure] --

Col. 6, line 46   Delete "[structure]" and substitute -- [structure] --

Col. 7, line 23   Delete "[structure]" and substitute -- [structure] --

UNITED STATES PATENT AND TRADEMARK OFFICE
CERTIFICATE OF CORRECTION

PATENT NO. : 4,840,946
DATED : June 20, 1989
INVENTOR(S) : Habich et al.

It is certified that error appears in the above-identified patent and that said Letters Patent is hereby corrected as shown below:

Col. 8, line 5    Delete " [structure] " and substitute -- [structure] --

Col. 8, line 37   Delete " [structure] " and substitute -- [structure] --

Col. 8, line 38   Delete " [structure] " and substitute -- [structure] --

Col. 9, line 5    Delete " [structure] " and substitute -- [structure] --

Col. 9, line 43   Delete " [structure] " and substitute -- [structure] --

Col. 11, line 24  After " example " delete "I"

Col. 11, line 31  Delete " heated " and substitute -- healed --

Col. 12, lines 36-37  Delete " polyvinylprrolidone " and substitute -- polyvinylpyrrolidone --

Col. 15, line 5   Delete " [structure] " and substitute -- [structure] --

Col. 15, line 46  Delete " [structure] " and substitute -- [structure] --

Col. 16, line 25  Delete " [structure] " and substitute -- [structure] --

UNITED STATES PATENT AND TRADEMARK OFFICE
CERTIFICATE OF CORRECTION

PATENT NO. : 4,840,946                                     Page 3 of 4

DATED      : June 20, 1989

INVENTOR(S) : Habich et al.

It is certified that error appears in the above-identified patent and that said Letters Patent is hereby corrected as shown below:

Col. 17, line 19  Delete "[structure with COOCH₂]" and substitute --[corrected structure with COOCH₂]--

Col. 17, line 56  Delete "[structure with COO-]" and substitute --[corrected structure with COO-]--

Col. 18, line 29  Delete "[structure with COONa]" and substitute --[corrected structure with COONa]--

Col. 18, line 58  Delete "[structure with COO-]" and substitute --[corrected structure with COO-]--

Col. 19, claim 1, line 18  Delete "[structure with COOR²]" and substitute --[corrected structure with COOR²]--

Col. 22, claim 4, line 21  Delete "[structure with COO-]" and substitute --[corrected structure with COO-]--

UNITED STATES PATENT AND TRADEMARK OFFICE
CERTIFICATE OF CORRECTION

PATENT NO. : 4,840,946

DATED : June 20, 1989

INVENTOR(S) : Habich, et al

Page 4 og 4

It is certified that error appears in the above-identified patent and that said Letters Patent is hereby corrected as shown below:

Col. 22, claim 5 line 34    Delete "[structure]"    and substitute --[structure]--

Col. 22, claim 6 line 47    Delete "[structure]"    and substitute --[structure]--

Signed and Sealed this

Twenty-fourth Day of September, 1991

Attest:

HARRY F. MANBECK, JR.

Attesting Officer

Commissioner of Patents and Trademarks